US012773532B2

(12) United States Patent
Hayden et al.

(10) Patent No.: US 12,773,532 B2
(45) Date of Patent: Oct. 27, 2026

(54) INFUSION SYSTEMS FOR IN-LINE DISINFECTION OF INFUSATES AND METHODS THEREOF

(71) Applicant: Bard Access Systems, Inc., Salt Lake City, UT (US)

(72) Inventors: Craig Hayden, Sandy, UT (US); Dustin Payne, West Jordan, UT (US); Timothy M. Snelling, Salt Lake City, UT (US); Matthew J. Prince, Herriman, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 725 days.

(21) Appl. No.: 18/104,448

(22) Filed: Feb. 1, 2023

(65) Prior Publication Data

US 2024/0252789 A1 Aug. 1, 2024

(51) Int. Cl.
*A61M 25/06* (2006.01)
*A61M 5/158* (2006.01)

(52) U.S. Cl.
CPC ............ *A61M 25/06* (2013.01); *A61M 5/158* (2013.01)

(58) Field of Classification Search
CPC .................. A61M 25/06; A61M 5/158; A61M 2025/0019; A61M 5/001;
(Continued)

(56) References Cited

U.S. PATENT DOCUMENTS 5,225,172 A 7/1993 Meyler et al.
5,441,504 A 8/1995 Pohndorf et al.
(Continued)

FOREIGN PATENT DOCUMENTS

CA 2199384 C 6/2006
CA 3080966 A1 11/2020
(Continued)

OTHER PUBLICATIONS

PCT/US2023/083089 filed Dec. 8, 2023, International Search Report and Written Opinion dated Jun. 3, 2024.
(Continued)

*Primary Examiner* — Theodore J Stigell
(74) *Attorney, Agent, or Firm* — Rutan & Tucker LLP

(57) ABSTRACT

An infusion system for in-line disinfection of a prepared infusate with UV light can include a vascular access device ("VAD") and a UV light ring. The VAD can include an intracorporeal conduit, one or more extracorporeal conduits fluidly connected to the intracorporeal conduit, a hub between a proximal portion of the intracorporeal conduit and one or more respective distal portions of the one-or-more extracorporeal conduits, and one or more respective connectors of the one-or-more extracorporeal conduits. The intracorporeal conduit is configured to be percutaneously inserted into a patient, and the extracorporeal conduit is configured to remain outside a body of the patient. The UV light ring can be configured to encircle a portion of an infusion lumen of the VAD and irradiate the prepared infusate within the infusion lumen with the UV light for infusing a disinfected infusate into the patient during an infusion of the patient.

22 Claims, 5 Drawing Sheets

(58) Field of Classification Search
CPC .......... A61M 2005/1581; A61M 39/16; A61M 2039/167; A61M 5/162; A61L 2/0047; A61L 2/10; A61L 2/26
See application file for complete search history.

(56) References Cited

U.S. PATENT DOCUMENTS

| | | | |
|---|---|---|---|
| 6,811,563 | B2 | 11/2004 | Savage, Jr. et al. |
| 6,908,460 | B2 | 6/2005 | DiStefano |
| 7,210,817 | B2 | 5/2007 | Lee et al. |
| 7,274,844 | B2 | 9/2007 | Walt et al. |
| 7,511,283 | B2 | 3/2009 | Chor |
| 8,197,087 | B2 | 6/2012 | Sobue et al. |
| 8,246,666 | B2 | 8/2012 | Pressler et al. |
| 8,372,128 | B2 | 2/2013 | Reuben |
| 8,387,405 | B2 | 3/2013 | Johnson |
| 8,556,950 | B2 | 10/2013 | Rioux et al. |
| 9,138,499 | B2 | 9/2015 | Bettles et al. |
| 9,592,374 | B2 | 3/2017 | Muse |
| 9,604,072 | B2 | 3/2017 | Brezinski |
| 9,925,285 | B1 | 3/2018 | Zaborsky et al. |
| 9,974,877 | B2 | 5/2018 | Bettles et al. |
| 9,981,052 | B2 | 5/2018 | Clynne et al. |
| 10,314,928 | B2 | 6/2019 | Dobrinsky et al. |
| 10,603,393 | B2 | 3/2020 | Rioux et al. |
| 10,610,609 | B2 | 4/2020 | Swaney et al. |
| 10,639,389 | B2 | 5/2020 | Paul et al. |
| 2002/0081228 | A1 | 6/2002 | Hui et al. |
| 2002/0168287 | A1 | 11/2002 | Eckhardt et al. |
| 2003/0018373 | A1 | 1/2003 | Eckhardt et al. |
| 2003/0036735 | A1 | 2/2003 | Jepson et al. |
| 2003/0063997 | A1 | 4/2003 | Fryer et al. |
| 2005/0101854 | A1 | 5/2005 | Larson et al. |
| 2007/0123825 | A1 | 5/2007 | King et al. |
| 2008/0027399 | A1 | 1/2008 | Harding et al. |
| 2008/0103560 | A1 | 5/2008 | Powell et al. |
| 2008/0257355 | A1 | 10/2008 | Rao et al. |
| 2008/0283769 | A1 | 11/2008 | Deshays |
| 2009/0177163 | A1 | 7/2009 | King et al. |
| 2010/0145721 | A1 | 6/2010 | Deshays |
| 2010/0296971 | A1 | 11/2010 | Gaska et al. |
| 2011/0144566 | A1 | 6/2011 | Dacey, Jr. et al. |
| 2012/0053512 | A1* | 3/2012 | Muse .................... A61M 39/16 604/20 |
| 2012/0116294 | A1 | 5/2012 | Boenig et al. |
| 2012/0143138 | A1 | 6/2012 | King et al. |
| 2012/0161032 | A1 | 6/2012 | Arcand et al. |
| 2012/0321509 | A1 | 12/2012 | Bak |
| 2013/0303996 | A1 | 11/2013 | Rasooly et al. |
| 2013/0323119 | A1* | 12/2013 | Alwan ...................... A61L 2/10 250/455.11 |
| 2013/0323120 | A1 | 12/2013 | Ma |
| 2014/0217307 | A1 | 8/2014 | Messina et al. |
| 2014/0257186 | A1 | 9/2014 | Kerr |
| 2015/0080851 | A1 | 3/2015 | Kurth et al. |
| 2015/0148734 | A1 | 5/2015 | Fewkes et al. |
| 2015/0157209 | A1 | 6/2015 | Dantus |
| 2015/0165185 | A1* | 6/2015 | Cohen ................... A61M 39/16 128/207.14 |
| 2015/0217010 | A1 | 8/2015 | Whitney |
| 2015/0231287 | A1 | 8/2015 | Lin et al. |
| 2015/0238747 | A1 | 8/2015 | Russo |
| 2015/0245810 | A1 | 9/2015 | Shine et al. |
| 2015/0273093 | A1 | 10/2015 | Holub et al. |
| 2015/0283277 | A1 | 10/2015 | Schafer et al. |
| 2016/0038621 | A1 | 2/2016 | Mctor et al. |
| 2016/0128526 | A1 | 5/2016 | Dobrinsky et al. |
| 2016/0151639 | A1 | 6/2016 | Scharf et al. |
| 2016/0303265 | A1 | 10/2016 | Coles |
| 2016/0310077 | A1 | 10/2016 | Hunter et al. |
| 2016/0317687 | A1 | 11/2016 | Dayton |
| 2017/0136209 | A1 | 5/2017 | Burnett et al. |
| 2017/0173251 | A1 | 6/2017 | Doyle et al. |
| 2017/0196478 | A1 | 7/2017 | Hunter |
| 2017/0216466 | A1 | 8/2017 | Dujowich et al. |
| 2017/0232123 | A1 | 8/2017 | Burapachaisri et al. |
| 2017/0252550 | A1 | 9/2017 | Wegener et al. |
| 2017/0281812 | A1 | 10/2017 | Dobrinsky et al. |
| 2017/0296142 | A1 | 10/2017 | Wodecki et al. |
| 2018/0280616 | A1 | 10/2018 | Witt et al. |
| 2018/0369560 | A1 | 12/2018 | Ball et al. |
| 2019/0111240 | A1 | 4/2019 | Fia et al. |
| 2019/0151587 | A1 | 5/2019 | Vazales et al. |
| 2019/0167825 | A1 | 6/2019 | Jones et al. |
| 2019/0192872 | A1 | 6/2019 | Schwarz et al. |
| 2019/0290360 | A1 | 9/2019 | Goodrich et al. |
| 2019/0290791 | A1 | 9/2019 | Baker et al. |
| 2019/0374668 | A1 | 12/2019 | Kopperschmidt et al. |
| 2020/0030473 | A1 | 1/2020 | Sugimoto et al. |
| 2020/0147248 | A1 | 5/2020 | Mintie et al. |
| 2020/0188543 | A1 | 6/2020 | Etter et al. |
| 2020/0254121 | A1 | 8/2020 | Swaney et al. |
| 2020/0261610 | A1 | 8/2020 | Rioux et al. |
| 2020/0324078 | A1 | 10/2020 | Motley et al. |
| 2020/0360549 | A1 | 11/2020 | Neveu et al. |
| 2020/0368379 | A1 | 11/2020 | Agarwal |
| 2021/0113725 | A1 | 4/2021 | Etter et al. |
| 2021/0154342 | A1 | 5/2021 | Canfield |
| 2021/0162081 | A1 | 6/2021 | Zhang et al. |
| 2021/0204818 | A1 | 7/2021 | Akins et al. |
| 2021/0236859 | A1 | 8/2021 | Park et al. |
| 2021/0338879 | A1 | 11/2021 | Davis et al. |
| 2022/0016439 | A1 | 1/2022 | Shah et al. |
| 2022/0088250 | A1 | 3/2022 | Baarman |
| 2022/0096677 | A1 | 3/2022 | Chan et al. |
| 2022/0152243 | A1 | 5/2022 | Koppen et al. |
| 2022/0175983 | A1 | 6/2022 | Wood et al. |
| 2022/0203007 | A1 | 6/2022 | Yuds et al. |
| 2022/0273837 | A1 | 9/2022 | Paul et al. |
| 2022/0313851 | A1 | 10/2022 | Subramanya et al. |
| 2022/0347456 | A1 | 11/2022 | Messerly |
| 2022/0387643 | A1 | 12/2022 | Baarman |
| 2023/0089985 | A1 | 3/2023 | Li et al. |
| 2023/0118324 | A1 | 4/2023 | Hong et al. |
| 2023/0233716 | A1 | 7/2023 | Yoon et al. |
| 2023/0293741 | A1 | 9/2023 | Matsui et al. |
| 2023/0301626 | A1 | 9/2023 | Howell |
| 2024/0115749 | A1 | 4/2024 | Payne et al. |
| 2024/0188859 | A1 | 6/2024 | Fellner et al. |
| 2024/0189467 | A1 | 6/2024 | Urry et al. |
| 2024/0226350 | A1 | 7/2024 | Payne et al. |
| 2024/0226351 | A1 | 7/2024 | Payne et al. |
| 2024/0226352 | A1 | 7/2024 | Fellner et al. |
| 2024/0335636 | A1 | 10/2024 | Laine et al. |
| 2024/0342325 | A1 | 10/2024 | Urry et al. |
| 2024/0350688 | A1 | 10/2024 | Prince |
| 2024/0374770 | A1 | 11/2024 | Durfee |
| 2025/0073360 | A1 | 3/2025 | Payne et al. |

FOREIGN PATENT DOCUMENTS

| | | | |
|---|---|---|---|
| CN | 104873219 | A | 9/2015 |
| CN | 106308727 | A | 1/2017 |
| CN | 108430533 | A | 8/2018 |
| CN | 208481489 | U | 2/2019 |
| CN | 209790441 | U | 12/2019 |
| CN | 213373944 | U | 6/2021 |
| CN | 213551294 | U | 6/2021 |
| CN | 113101207 | A | 7/2021 |
| CN | 213642120 | U | 7/2021 |
| CN | 113476076 | A | 10/2021 |
| CN | 215426269 | U | 1/2022 |
| EP | 3195805 | A1 | 7/2017 |
| EP | 3738617 | A2 | 11/2020 |
| JP | 2005198761 | A | 7/2005 |
| KR | 20110050077 | A | 5/2011 |
| KR | 20140003473 | U | 6/2014 |
| KR | 101654328 | B1 | 9/2016 |
| KR | 20220000634 | U | 3/2022 |
| KR | 20220063891 | A | 5/2022 |
| KR | 102452057 | B1 | 10/2022 |
| WO | 9607451 | A2 | 3/1996 |
| WO | 2011068545 | A1 | 6/2011 |
| WO | 2011107540 | A1 | 9/2011 |

(56) References Cited

FOREIGN PATENT DOCUMENTS

| | | | |
|---|---|---|---|
| WO | 2013134421 | A1 | 9/2013 |
| WO | 2014165854 | A1 | 10/2014 |
| WO | 2015157518 | A1 | 10/2015 |
| WO | 2019108431 | A1 | 6/2019 |
| WO | 2020115230 | A1 | 6/2020 |
| WO | 2020167843 | A1 | 8/2020 |
| WO | 2021146667 | A1 | 7/2021 |
| WO | 2021146701 | A1 | 7/2021 |
| WO | 2021157769 | A1 | 8/2021 |
| WO | 2022036886 | A1 | 2/2022 |
| WO | 2022046138 | A1 | 3/2022 |
| WO | 2022200038 | A2 | 9/2022 |
| WO | 2022232479 | A1 | 11/2022 |
| WO | 2023183426 | A1 | 9/2023 |
| WO | 2024081335 | A1 | 4/2024 |
| WO | 2024124112 | A1 | 6/2024 |
| WO | 2024129817 | A1 | 6/2024 |
| WO | 2024/151420 | A1 | 7/2024 |
| WO | 2024/151421 | A1 | 7/2024 |
| WO | 2024/151648 | A1 | 7/2024 |
| WO | 2024163670 | A1 | 8/2024 |
| WO | 2024211387 | A1 | 10/2024 |
| WO | 2024215932 | A1 | 10/2024 |
| WO | 2024220523 | A1 | 10/2024 |
| WO | 2024233805 | A1 | 11/2024 |
| WO | 2025049496 | A1 | 3/2025 |

OTHER PUBLICATIONS

PCT/US2023/085839 filed Dec. 22, 2023, International Search Report and Written Opinion dated Jun. 11, 2024.

PCT/US2024/013858 filed Jan. 31, 2024, International Search Report and Written Opinion dated May 22, 2024.

Cabral, Joao, and Rodrigues A. G. "Blue light disinfection in hospital infection control: advantages, drawbacks, and pitfalls." Antibiotics 8.2 (2019): 58.

Changtong, Chuchawin, et al. "A porphyrin molecule that generates, traps, stores, and releases singlet oxygen." Journal of Photochemistry and Photobiology A: Chemistry 260 (2013): 9-13.

Halstead, Fenella D., et al. "The potential of visible blue light (405 nm) as a novel decontamination strategy for carbapenemase-producing enterobacteriaceae (CPE)." Antimicrobial Resistance & Infection Control 8.1 (2019): 1-8.

Tsen, Shaw-Wei David, et al. "Inactivation of multidrug-resistant bacteria and bacterial spores and generation of high-potency bacterial vaccines using ultrashort pulsed lasers." Journal of Biophotonics 15.2 (2022): e202100207.

PCT/US2023/015961 filed Mar. 22, 2023, International Search Report and Written Opinion dated Jul. 17, 2023.

PCT/US2023/034981 filed Oct. 11, 2023, International Search Report and Written Opinion dated Dec. 11, 2023.

CS Medical "Caring for TEE Probes the Right Way" Mar. 17, 2022.

PCT/US2023/085837 filed Dec. 22, 2023, International Preliminary Report on Patentability dated Jul. 3, 2025.

PCT/US2024/013858 filed Jan. 31, 2024 International Preliminary Report on Patentability dated Jul. 31, 2025.

PCT/US2024/022801 filed Apr. 4, 2024, International Search Report and Written Opinion dated Sep. 6, 2024.

U.S. Appl. No. 17/732,614, filed Apr. 29, 2022 Final Office Action dated Sep. 4, 2025.

U.S. Appl. No. 17/963,594, filed Oct. 11, 2022 Non-Final Office Action dated Aug. 22, 2025.

U.S. Appl. No. 18/077,994, filed Dec. 8, 2022 Non-Final Office Action dated Jul. 30, 2025.

U.S. Appl. No. 18/080,624, filed Dec. 13, 2022 Non-Final Office Action dated Oct. 1, 2025.

U.S. Appl. No. 18/080,624, filed Dec. 13, 2022 Restriction Requirement dated Jul. 10, 2025.

U.S. Appl. No. 18/094,760, filed Jan. 9, 2023 Non-Final Office Action dated Sep. 10, 2025.

U.S. Appl. No. 18/094,760, filed Jan. 9, 2023 Restriction Requirement dated Jun. 18, 2025.

U.S. Appl. No. 18/094,785, filed Jan. 9, 2023 Non-Final Office Action dated Aug. 27, 2025.

U.S. Appl. No. 18/094,785, filed Jan. 9, 2023 Restriction Requirement dated Jun. 18, 2025.

U.S. Appl. No. 18/095,469, filed Jan. 10, 2023 Non-Final Office Action dated Sep. 8, 2025.

U.S. Appl. No. 18/195,018, filed May 9, 2023 Non-Final Office Action dated Jul. 3, 2025.

PCT/US2023/083767 filed Dec. 13, 2023, International Search Report and Written Opinion dated Apr. 25, 2024.

PCT/US2023/085837 filed Dec. 22, 2023, International Search Report and Written Opinion dated Apr. 9, 2024.

PCT/US2024/010902 filed Jan. 9, 2024, International Search Report and Written Opinion dated Apr. 24, 2024.

Changtong et al., "A porphyrin molecule that generates, traps, stores, and releases singlet oxygen.", Journal of Photochemistry and Photobiology A: Chemistry 260 (Sep. 13, 2013).

PCT/US2022/026888 filed Apr. 29, 2022 International Search Report and Writtent Opinion dated Jul. 29, 2022.

Tsen et al., "Inactivation of multidrug-resistant bacteria and bacterial spores and generation of high-potency bacterial vaccines using ultrashort pulsed lasers." Journal of Biophotonics, 2021.

PCT/US2024/024136 filed Apr. 11, 2024, International Search Report and Written Opinion dated Sep. 18, 2024.

PCT/US2024/024969 filed Apr. 17, 2024, International Search Report and Written Opinion dated Sep. 27, 2024.

PCT/US2024/028630 filed May 9, 2024, International Search Report and Written Opinion dated Sep. 18, 2024.

PCT/US2024/044069 filed Aug. 27, 2024, International Search Report and Written Opinion dated Jan. 31, 2025.

U.S. Appl. No. 17/732,614, filed Apr. 29, 2022 Non-Final Office Action dated May 9, 2025.

U.S. Appl. No. 17/963,594, filed Oct. 11, 2022 Restriction Requirement dated Jun. 3, 2025.

U.S. Appl. No. 18/125,029, filed Mar. 22, 2023 Notice of Allowance dated Dec. 18, 2024.

U.S. Appl. No. 17/732,614, filed Apr. 29, 2022 Advisory Action Nov. 14, 2025.

U.S. Appl. No. 17/732,614, filed Apr. 29, 2022 Non-Final Office Action dated Jan. 28, 2026.

U.S. Appl. No. 17/963,594, filed Oct. 11, 2022 Final Office Action dated Jan. 8, 2026.

U.S. Appl. No. 18/080,624, filed Dec. 13, 2022 Final Office Action dated Jan. 30, 2026.

U.S. Appl. No. 18/095,469, filed Jan. 10, 2023 Notice of Allowance dated Jan. 7, 2026.

U.S. Appl. No. 18/132,261, filed Apr. 7, 2023 Restriction Requirement dated Nov. 10, 2025.

U.S. Appl. No. 18/136,111, filed Apr. 18, 2023 Notice of Allowance dated Dec. 23, 2025.

U.S. Appl. No. 18/195,018, filed May 9, 2023 Final Office Action dated Oct. 23, 2025.

U.S. Appl. No. 17/963,594, filed Oct. 11, 2022 Advisory Action dated Mar. 6, 2026.

U.S. Appl. No. 17/963,594, filed Oct. 11, 2022 Non-Final Office Action dated Apr. 27, 2026.

U.S. Appl. No. 18/077,994, filed Dec. 8, 2022 Advisory Action dated Apr. 23, 2026.

U.S. Appl. No. 18/077,994, filed Dec. 8, 2022 Final Office Action dated Feb. 12, 2026.

U.S. Appl. No. 18/080,624, filed Dec. 13, 2022 Advisory Action dated Apr. 7, 2026.

U.S. Appl. No. 18/094,760, filed Jan. 9, 2023 Final Office Action dated Mar. 19, 2026.

U.S. Appl. No. 18/094,785, filed Jan. 9, 2023 Final Office Action dated Mar. 27, 2026.

U.S. Appl. No. 18/132,261, filed Apr. 7, 2023 Non-Final Office Action dated Feb. 9, 2026.

U.S. Appl. No. 18/195,018, filed May 9, 2023 Non-Final Office Action dated Apr. 9, 2026.

(56) References Cited

OTHER PUBLICATIONS

U.S. Appl. No. 18/239,048, filed Aug. 28, 2023 Restriction Requirement dated Mar. 3, 2026.
U.S. Appl. No. 18/633,354, filed Apr. 11, 2024 Non-Final Office Action dated May 6, 2026.
U.S. Appl. No. 17/732,614, filed Apr. 29, 2022 Final Office Action dated Jun. 1, 2026.
U.S. Appl. No. 18/077,994, filed Dec. 8, 2022 Non-Final Office Action dated Jun. 12, 2026.
U.S. Appl. No. 18/080,624, filed Dec. 13, 2022 Non-Final Office Action dated Aug. 7, 2026.
U.S. Appl. No. 18/094,760, filed Jan. 9, 2023 Advisory Action dated May 21, 2026.
U.S. Appl. No. 18/094,760, filed Jan. 9, 2023 Non-Final Office Action dated Jul. 1, 2026.
U.S. Appl. No. 18/094,785, filed Jan. 9, 2023 Notice of Allowance dated Jun. 15, 2026.
U.S. Appl. No. 18/132,261, filed Apr. 7, 2023 Final Office Action dated Jul. 16, 2026.
U.S. Appl. No. 18/239,048, filed Aug. 28, 2023 Non-Final Office Action dated Jun. 18, 2026.

* cited by examiner

INFUSION SYSTEMS FOR IN-LINE DISINFECTION OF INFUSATES AND METHODS THEREOF

BACKGROUND

Ultraviolet ("UV") light is known to damage bacteria and their endotoxins, and such knowledge has been implemented in various disinfection systems for disinfecting medical devices with UV light including UV disinfection cabinets and handheld UV lamps. While existing disinfection systems might be effective for disinfecting medical devices with UV light before use of the medical devices, such existing disinfection systems are not suitable for real-time disinfection with UV light during a medical procedure. It follows that the existing disinfection systems are also not suitable for real-time, in-line disinfection of supplier- or clinician-prepared infusate with UV light during an infusion, which disinfection is desirable for reducing infusion-related blood infections.

Disclosed herein are infusion systems for in-line disinfection of prepared infusates with UV light and methods thereof.

SUMMARY

Disclosed herein is an infusion system for in-line disinfection of a prepared infusate with UV light. The infusion system includes a vascular access device ("VAD") and a UV light ring. The VAD includes an intracorporeal conduit, one or more extracorporeal conduits fluidly connected to the intracorporeal conduit, a hub between a proximal portion of the intracorporeal conduit and one or more respective distal portions of the one-or-more extracorporeal conduits, and one or more respective connectors of the one-or-more extracorporeal conduits. The intracorporeal conduit is configured to be percutaneously inserted into a patient, and the extracorporeal conduit is configured to remain outside a body of the patient. The UV light ring is configured to encircle a portion of an infusion lumen of the VAD. The UV light ring is also configured to irradiate the prepared infusate within the infusion lumen with the UV light for infusing a disinfected infusate into the patient during an infusion of the patient.

In some embodiments, the UV light ring is removably or fixedly coupled about an abluminal surface of the intracorporeal conduit, an extracorporeal conduit of the one-or-more extracorporeal conduits, a hub conduit of one or more hub conduits respectively fluidly connecting the one-or-more extracorporeal conduits to the intracorporeal conduit, or a connector of the one-or-more connectors.

In some embodiments, the UV light ring is removably coupled about the abluminal surface of the intracorporeal conduit, the extracorporeal conduit, the hub conduit, or the connector. The UV light ring is configured to automatically adjust its size in accordance with a size of the intracorporeal conduit, the extracorporeal conduit, the hub conduit, or the connector.

In some embodiments, the intracorporeal conduit, the extracorporeal conduit, the hub conduit, or the connector about which the UV light ring is fixedly or removably coupled is formed of a material that does not appreciably reflect or absorb the UV light from the UV light ring.

In some embodiments, the UV light ring is integrated into a luminal surface of the intracorporeal conduit, an extracorporeal conduit of the one-or-more extracorporeal conduits, a hub conduit of one or more hub conduits respectively fluidly connecting the one-or-more extracorporeal conduits to the intracorporeal conduit, or a connector of the one-or-more connectors.

In some embodiments, the VAD further comprises a fixed or removable internal power source and electronic circuitry between the internal power source and the UV light ring. The electronic circuitry is configured to supply power to the UV light ring from the internal power source.

In some embodiments, the infusion system further includes an electrical cable and electronic circuitry between the electrical cable and the UV light ring. The electrical cable is configured to connect to an external power source. The electronic circuitry is configured to supply power to the UV light ring.

In some embodiments, the infusion system further comprises an indicator light operably connected to the electronic circuitry. The indicator light is configured to emit visible light when the UV light ring emits the UV light.

In some embodiments, the UV light ring is configured to automatically emit the UV light upon an activation event selected from an assembly step while assembling the VAD, a connecting step while connecting the VAD to an infusion bag containing the prepared infusate, or an initiating step of infusing the prepared infusate into the patient through the infusion lumen.

In some embodiments, the VAD is a catheter. The intracorporeal conduit, the one-or-more extracorporeal conduits, the hub, and the one-or-more connectors corresponds to a catheter tube, one or more extension legs, a catheter hub, and one or more Luer connectors of the catheter, respectively.

In some embodiments, the VAD is a Huber needle set. The intracorporeal conduit, the one-or-more extracorporeal conduits, the hub, and the one-or-more connectors corresponds to a needle, an extension tube, a needle hub, and a Luer connector of the Huber needle set, respectively.

Also disclosed herein is a method of an infusion system for in-line disinfection of a prepared infusate with UV light. The method includes a VAD-obtaining step, a VAD-connecting step, and an infusing step. The VAD-obtaining step includes obtaining a VAD of the infusion system. The VAD includes an intracorporeal conduit, one or more extracorporeal conduits fluidly connected to the intracorporeal conduit, a hub between a proximal portion of the intracorporeal conduit and one or more respective distal portions of the one-or-more extracorporeal conduits, and one or more respective connectors of the one-or-more extracorporeal conduits. The intracorporeal conduit is configured to be percutaneously inserted into a patient, and the extracorporeal conduit is configured to remain outside a body of the patient. The VAD-connecting step includes connecting the VAD to an infusion bag containing a prepared infusate. The infusing step includes infusing the patient with a disinfected infusate. The disinfected infusate results from irradiation of the prepared infusate within an infusion lumen of the VAD by the UV light from a UV light ring encircling a portion of the infusion lumen.

In some embodiments, the UV light ring is removably or fixedly coupled about an abluminal surface of the intracorporeal conduit, an extracorporeal conduit of the one-or-more extracorporeal conduits, a hub conduit of one or more hub conduits respectively fluidly connecting the one-or-more extracorporeal conduits to the intracorporeal conduit, or a connector of the one-or-more connectors.

In some embodiments, the method further includes a light ring-placing step. The light ring-placing step includes placing the UV light ring over the abluminal surface of the intracorporeal conduit, the extracorporeal conduit, the hub conduit, or the connector, thereby removably coupling the UV light ring to the VAD. The UV light ring is configured to automatically adjust its size in accordance with a size of the intracorporeal conduit, the extracorporeal conduit, the hub conduit, or the connector.

In some embodiments, the intracorporeal conduit, the extracorporeal conduit, the hub conduit, or the connector about which the UV light ring is fixedly or removably coupled is formed of a material that does not appreciably reflect or absorb the UV light from the UV light ring.

In some embodiments, the UV light ring is integrated into a luminal surface of the intracorporeal conduit, an extracorporeal conduit of the one-or-more extracorporeal conduits, a hub conduit of one or more hub conduits respectively fluidly connecting the one-or-more extracorporeal conduits to the intracorporeal conduit, or a connector of the one-or-more connectors.

In some embodiments, the VAD further comprises a fixed or removable internal power source and electronic circuitry between the internal power source and the UV light ring. The electronic circuitry is configured to supply power to the UV light ring from the internal power source.

In some embodiments, the method further includes a cable-connecting step. The cable-connecting step includes connecting an electrical cable to an external power source. Electronic circuitry between the electrical cable and the UV light ring is configured to supply power to the UV light ring.

In some embodiments, an indicator light operably connected to the electronic circuitry is configured to emit visible light when the UV light ring emits the UV light.

In some embodiments, the UV light ring is configured to automatically emit the UV light upon an activation event selected from an assembly step while assembling the VAD, the VAD-connecting step while connecting the VAD to the infusion bag, or initiation of the infusing step of infusing the patient with the disinfected infusate.

In some embodiments, the VAD is a catheter. The intracorporeal conduit, the one-or-more extracorporeal conduits, the hub, and the one-or-more connectors corresponds to a catheter tube, one or more extension legs, a catheter hub, and one or more Luer connectors of the catheter, respectively.

In some embodiments, the VAD is a Huber needle set. The intracorporeal conduit, the one-or-more extracorporeal conduits, the hub, and the one-or-more connectors corresponds to a needle, an extension tube, a needle hub, and a Luer connector of the Huber needle set, respectively.

In some embodiments, the VAD is a Huber needle set. The intracorporeal conduit, the one-or-more extracorporeal conduits, the hub, and the one-or-more connectors corresponds to a needle, an extension tube, a needle hub, and a Luer connector of the Huber needle set, respectively.

These and other features of the concepts provided herein will become more apparent to those of skill in the art in view of the accompanying drawings and following description, which describe particular embodiments of such concepts in greater detail.

DRAWINGS

DESCRIPTION

Figure 1:
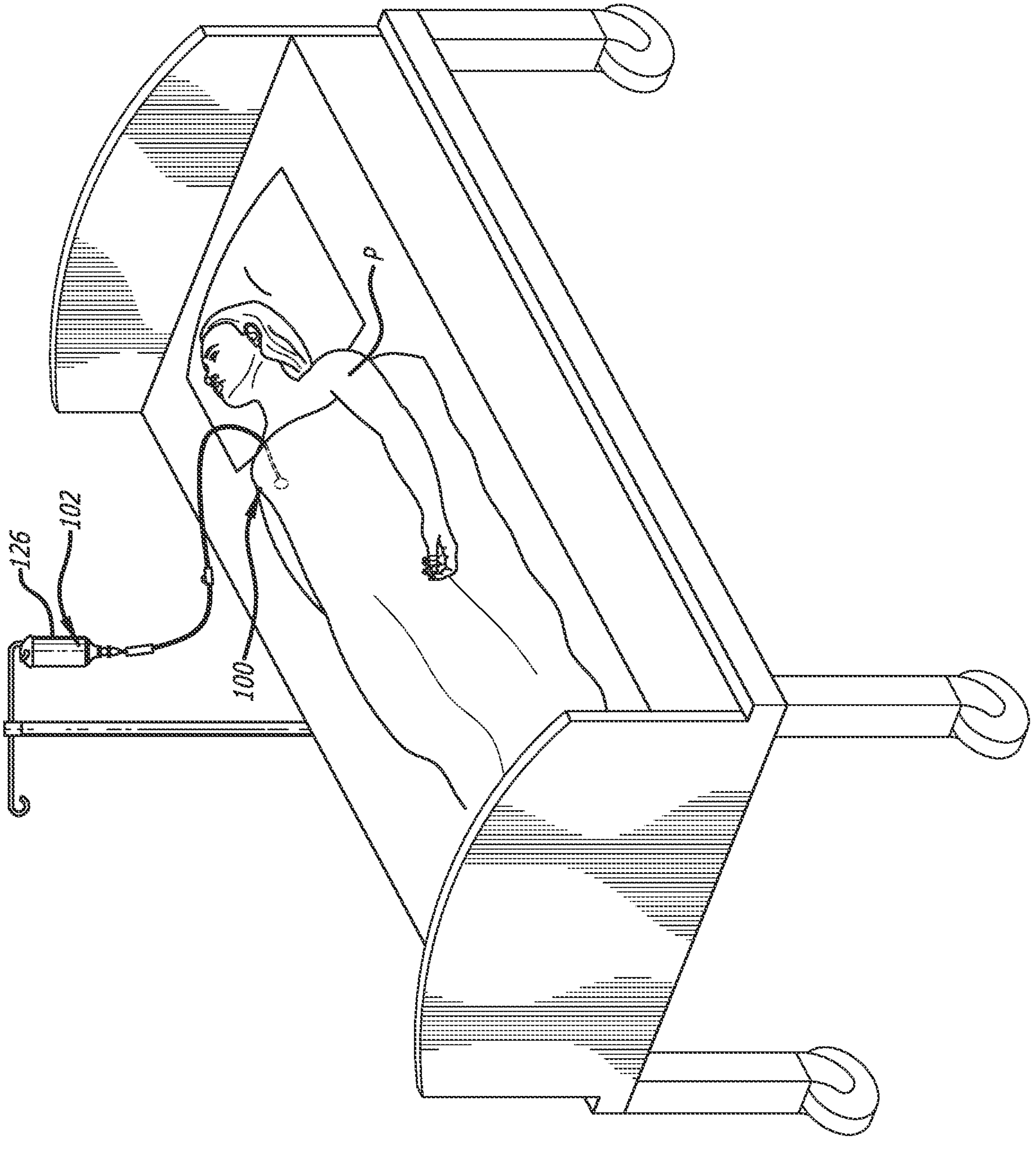
FIG. 1 illustrates infusion of a patient with an infusion system for in-line disinfection of a prepared infusate with UV light in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. In addition, any of the foregoing features or steps can, in turn, further include one or more features or steps unless indicated otherwise. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

"Proximal" is used to indicate a portion, section, piece, element, or the like of a medical device intended to be near or relatively nearer to a clinician when the medical device is used on a patient. For example, a "proximal portion" or "proximal section" of the medical device includes a portion or section of the medical device intended to be near the clinician when the medical device is used on the patient. Likewise, a "proximal length" of the medical device includes a length of the medical device intended to be near the clinician when the medical device is used on the patient. A "proximal end" of the medical device is an end of the medical device intended to be near the clinician when the medical device is used on the patient. The proximal portion, the proximal section, or the proximal length of the medical device need not include the proximal end of the medical device. Indeed, the proximal portion, the proximal section, or the proximal length of the medical device can be short of the proximal end of the medical device. However, the proximal portion, the proximal section, or the proximal length of the medical device can include the proximal end of the medical device. Should context not suggest the proximal portion, the proximal section, or the proximal length of the medical device includes the proximal end of the medical device, or if it is deemed expedient in the following description, "proximal portion," "proximal section," or "proximal length" can be modified to indicate such a portion, section, or length includes an end portion, an end section, or an end length of the medical device for a "proximal end portion," a "proximal end section," or a "proximal end length" of the medical device, respectively.

"Distal" is used to indicate a portion, section, piece, element, or the like of a medical device intended to be near, relatively nearer, or even in a patient when the medical device is used on the patient. For example, a "distal portion" or "distal section" of the medical device includes a portion or section of the medical device intended to be near, relatively nearer, or even in the patient when the medical device is used on the patient. Likewise, a "distal length" of the medical device includes a length of the medical device intended to be near, relatively nearer, or even in the patient when the medical device is used on the patient. A "distal end" of the medical device is an end of the medical device intended to be near, relatively nearer, or even in the patient when the medical device is used on the patient. The distal portion, the distal section, or the distal length of the medical device need not include the distal end of the medical device. Indeed, the distal portion, the distal section, or the distal length of the medical device can be short of the distal end of the medical device. However, the distal portion, the distal section, or the distal length of the medical device can include the distal end of the medical device. Should context not suggest the distal portion, the distal section, or the distal length of the medical device includes the distal end of the medical device, or if it is deemed expedient in the following description, "distal portion," "distal section," or "distal length" can be modified to indicate such a portion, section, or length includes an end portion, an end section, or an end length of the medical device for a "distal end portion," a "distal end section," or a "distal end length" of the medical device, respectively.

Unless defined otherwise, all technical and scientific terms used herein have the same meaning as commonly understood by those of ordinary skill in the art.

Again, UV light is known to damage bacteria and their endotoxins, and such knowledge has been implemented in various disinfection systems for disinfecting medical devices with UV light including UV disinfection cabinets and handheld UV lamps. While existing disinfection systems might be effective for disinfecting medical devices with UV light before use of the medical devices, such existing disinfection systems are not suitable for real-time disinfection with UV light during a medical procedure. It follows that the existing disinfection systems are also not suitable for real-time, in-line disinfection of supplier- or clinician-prepared infusate with UV light during an infusion, which disinfection is desirable for reducing infusion-related blood infections.

Disclosed herein are infusion systems for in-line disinfection of prepared infusates with UV light and methods thereof.

Infusion Systems

Figure 2:
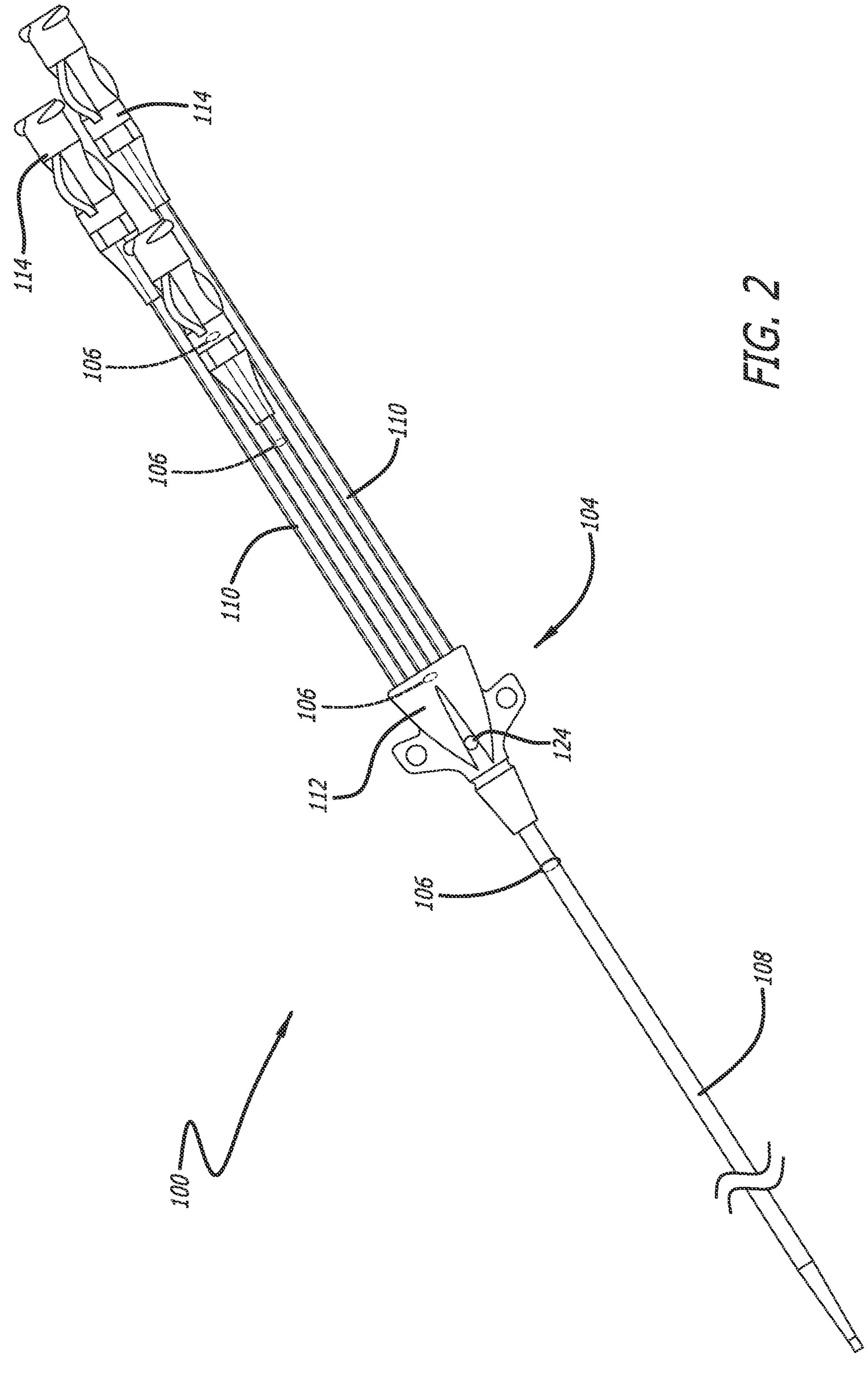
FIG. 2 illustrates a central venous catheter for a VAD of the infusion system in accordance with some embodiments.
Figure 3:
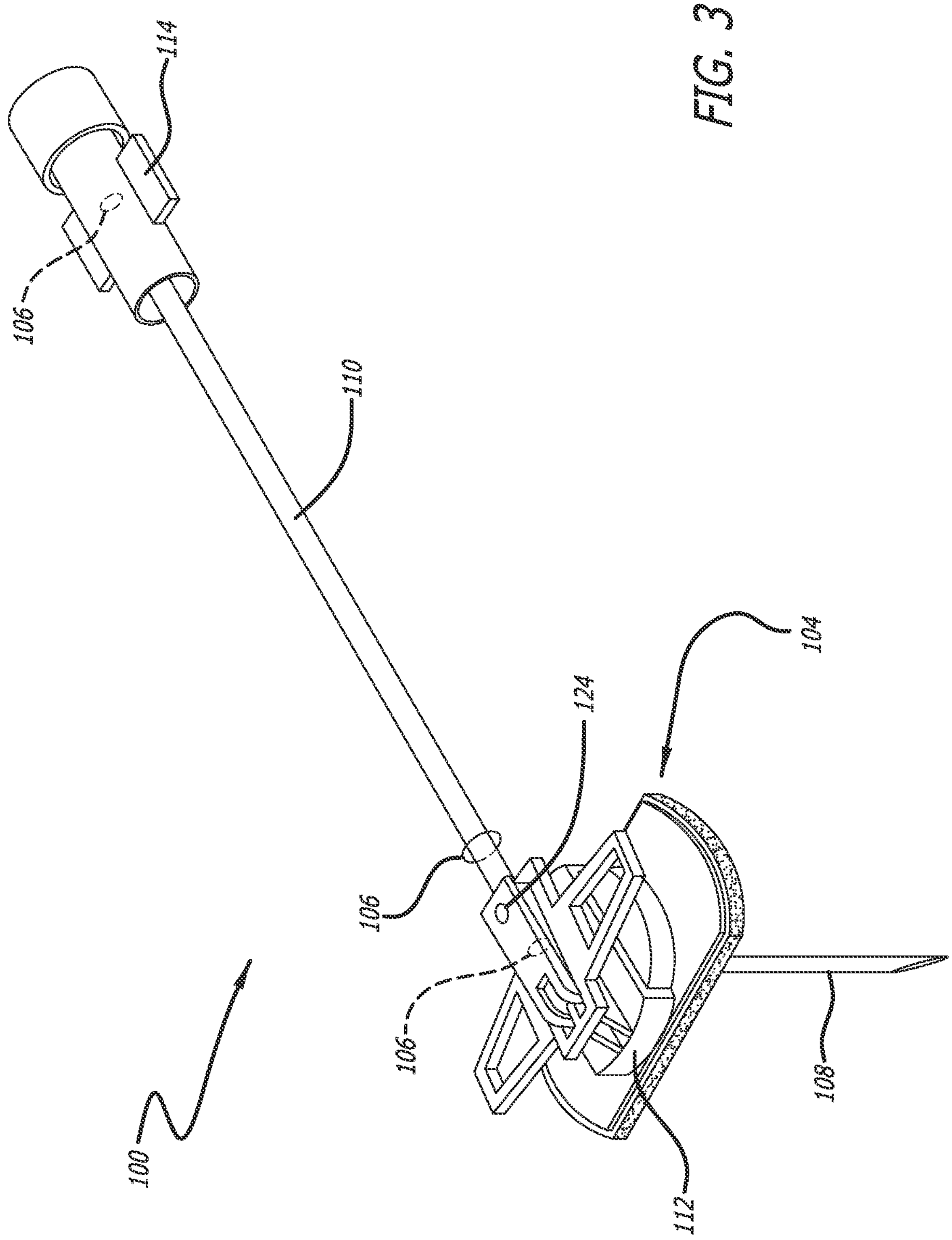
FIG. 3 illustrates a Huber needle set for another VAD of the infusion system in accordance with some embodiments.

FIG. 1 illustrates infusion of a patient P with an infusion system 100 for in-line disinfection of a prepared infusate 102 with UV light ("hv" in FIGS. 4 and 5) in accordance with some embodiments. FIGS. 2 and 3 respectively illustrate a central venous catheter and a Huber needle set for a VAD 104 of the infusion system 100 in accordance with some embodiments.

As shown, the infusion system 100 includes the VAD 104 and a UV light ring 106 either integrated with the VAD 104 or separate therefrom but configured to couple to the VAD 104. Notably, several options for placement of the UV light ring 106 about or within the VAD 104 are shown in FIGS. 2 and 3. However, it should be understood the VAD 104 can include two or more of such UV light rings, as desired.

The VAD 104 includes an intracorporeal conduit 108, one or more extracorporeal conduits 110 fluidly connected to the intracorporeal conduit 108, a hub 112 between a proximal portion of the intracorporeal conduit 108 and one or more respective distal portions of the one-or-more extracorporeal conduits 110, and one or more respective connectors 114 of the one-or-more extracorporeal conduits 110. At least a portion of the intracorporeal conduit 108 is configured to be percutaneously inserted into the patient P. In contrast, an entirety of the extracorporeal conduit is configured to remain outside a body of the patient P.

FIG. 2 shows the VAD 104 can be a central venous catheter; however, the VAD 104 can be any of a number of other catheters including a peripherally inserted central catheter, a peripheral intravenous catheter, or the like. With respect to the central venous catheter shown in in FIG. 2, the intracorporeal conduit 108, the one-or-more extracorporeal conduits 110, the hub 112, and the one-or-more connectors 114 correspond to a catheter tube, one or more extension legs, a catheter hub, and one or more Luer connectors of the central venous catheter, respectively.

FIG. 3 shows the VAD 104 can be a Huber needle set for accessing an implanted vascular access port like that alluded to in FIG. 1; however, the VAD 104 can be any of a number of other infusion sets. With respect to the Huber needle set shown in in FIG. 3, the intracorporeal conduit 108, the one-or-more extracorporeal conduits 110, the hub 112, and the one-or-more connectors 114 corresponds to a needle, an extension tube, a needle hub, and a Luer connector of the Huber needle set, respectively.

Again, the UV light ring 106 is either integrated with the VAD 104 or separate therefrom but configured to couple to the VAD 104. Regardless, the UV light ring 106 is configured to encircle a portion of an infusion lumen 116 of the VAD 104. Further, the UV light ring 106 is configured to irradiate the prepared infusate 102, when present, within the infusion lumen 116 of the VAD 104 with the UV light therefrom, thereby allowing a disinfected infusate to be infused into the patient P during an infusion of the patient P.

Notably, the UV light ring 106 can be configured to emit the UV light in a range from about 100 nm to about 280 nm, which corresponds to the so-called UVC range; however, the UV light ring 106 need not be limited to emission the UVC range. Indeed, the UV light ring 106 can be configured to emit the UV light anywhere in the UV portion of the electromagnetic spectrum. In an example, the UV light ring 106 can be alternatively configured to emit the UV light in a range from about 280 nm to about 315 nm, which corresponds to the so-called UVB range. In another example, the UV light ring 106 can be alternatively configured to emit the UV light in a range from about 315 nm to about 400 nm, which corresponds to the so-called UVA range. In consideration of the UV light ring 106 being configured to emit the UV light in the UVC range, the UV light ring 106 can include one or more light-emitting diodes ("LEDs") arranged in a sealed annular conduit 118, which LEDs can independently have emission peaks anywhere in the UVC range such as 265 nm, 273 nm, or 280 nm. Such LEDs advantageously allow the UV light emitted from the UV light ring 106 to be selected to provide a broader range (e.g., 265 nm to 280 nm), a narrower range (e.g., 265 nm to 273 nm or 273 nm to 280 nm), or even a gapped range (e.g., 265 nm to 280 nm with a gap around 273 nm), as desired, to accommodate components of the VAD 104 formed of UV light-sensitive materials or even medicaments including UV light-sensitive molecular entities. That said, at least the VAD 104 including the UV light ring 106 integrated therein or fixedly coupled thereto, and, particularly, the component of the VAD 104 including the UV light ring 106, can be formed of one or more materials sufficiently inert to the UV light of the UV light ring 106.

Figure 4:
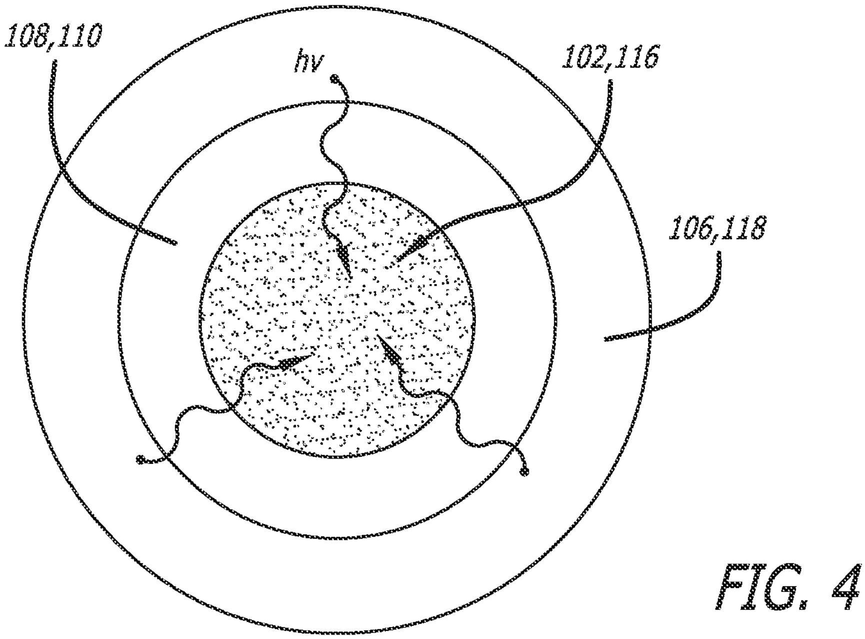
FIG. 4 illustrates a transverse cross-section of a UV light ring around an abluminal surface of the VAD in accordance with some embodiments.

FIG. 4 illustrates a transverse cross-section of the UV light ring 106 around an abluminal surface of the VAD 104 in accordance with some embodiments.

As shown, the UV light ring 106 can be removably or fixedly coupled about the abluminal surface of the intracorporeal conduit 108 but proximal of a portion of the intracorporeal conduit 108 intended to be within the patient P. Alternatively, the UV light ring 106 can be removably or fixedly coupled about an abluminal surface of an extracorporeal conduit of the one-or-more extracorporeal conduits 110, a hub conduit of one or more hub conduits respectively fluidly connecting the one-or-more extracorporeal conduits 110 to the intracorporeal conduit 108, or a connector of the one-or-more connectors 114. In consideration of the UV light ring 106 being removably coupled about the abluminal surface of the intracorporeal conduit 108, the extracorporeal conduit, the hub conduit, or the connector, the UV light ring 106 can be configured to automatically adjust its size in accordance with a size of the intracorporeal conduit 108, the extracorporeal conduit, the hub conduit, or the connector. However, in other embodiments the UV light ring 106 is manufactured in different sizes for coupling the UV light ring 106 about the abluminal surface of the intracorporeal conduit 108, the extracorporeal conduit, the hub conduit, or the connector of larger or smaller VADs. Notably, the intracorporeal conduit 108, the extracorporeal conduit, the hub conduit, or the connector about which the UV light ring 106 is fixedly or removably coupled should be formed of a material that does not appreciably reflect or absorb the UV light from the UV light ring 106.

Figure 5:
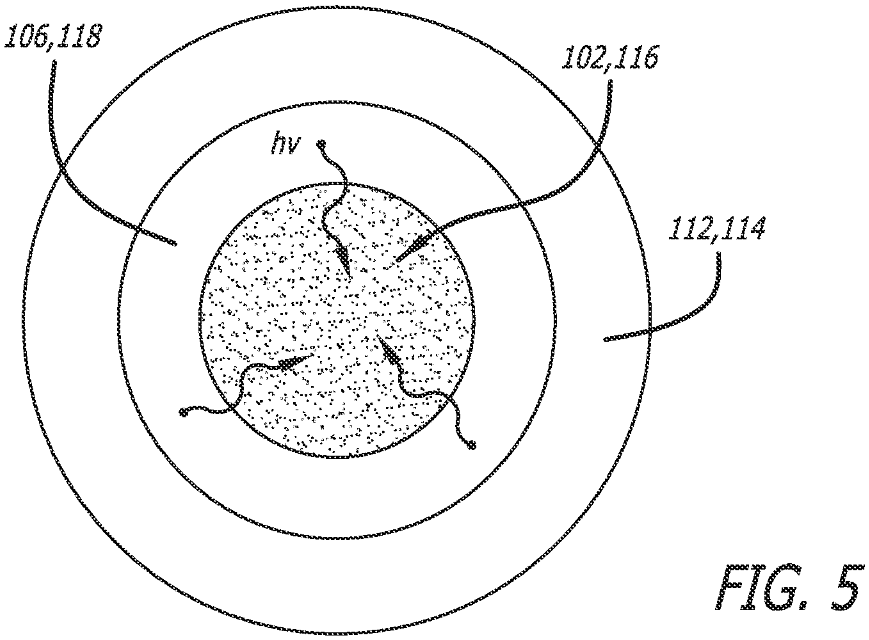
FIG. 5 illustrates a transverse cross-section of a UV light ring integrated into a luminal surface of the VAD in accordance with some embodiments.

FIG. 5 illustrates a transverse cross-section of the UV light ring 106 integrated into a luminal surface of the VAD 104 in accordance with some embodiments.

As shown, the UV light ring 106 can be integrated into the luminal surface of the intracorporeal conduit 108, an extracorporeal conduit of the one-or-more extracorporeal conduits 110, a hub conduit of one or more hub conduits respectively fluidly connecting the one-or-more extracorporeal conduits 110 to the intracorporeal conduit 108, or a connector of the one-or-more connectors 114. When the UV light ring 106 is integrated into the luminal surface of the intracorporeal conduit 108, the extracorporeal conduit, the hub conduit, or the connector, the UV light is advantageously contained, thereby reducing or eliminating clinician or patient exposure.

Figure 6:
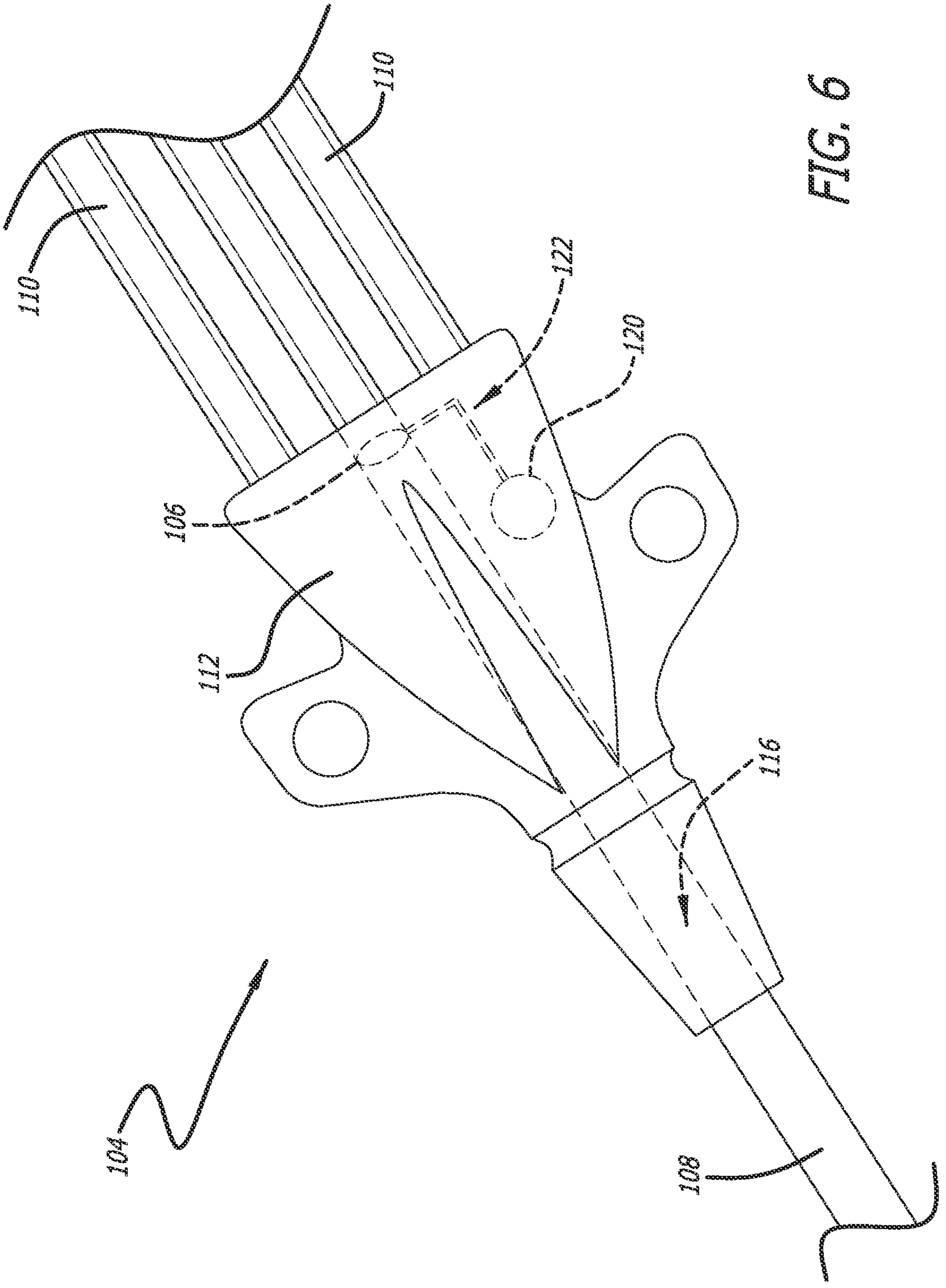
FIG. 6 illustrates an internal power source and electronic circuitry between the internal power source and the UV light ring in accordance with some embodiments.

FIG. 6 illustrates an internal power source 120 (e.g., battery) and electronic circuitry 122 in accordance with some embodiments.

As shown, the VAD 104 can include a fixed or removable internal power source for the internal power source 120 with the electronic circuitry 122 between the internal power source 120 and the UV light ring 106.

Alternatively, the infusion system 100 or the VAD 104, itself, can include an electrical cable and the electronic circuitry 122 between the electrical cable and the UV light ring 106. The electrical cable is configured with a plug to connect to an external power source. Whether the VAD 104 includes the internal power source 120 or utilizes the electrical cable, the electronic circuitry 122 is configured to supply power to the UV light ring 106 from the power source.

As shown in FIGS. 2 and 3, the infusion system 100 or the VAD 104, itself, can include an indicator light 124 operably connected to the electronic circuitry 122. Being that the UV light is invisible to human eyes, the indicator light 124 is configured to emit visible light as an indicator of the UV light when the UV light ring 106 emits the UV light.

Notably, as set forth in the method below, the UV light ring 106 can be configured to automatically emit the UV light upon an activation event selected from an assembly step while assembling the VAD 104 (e.g., coupling the UV light ring 106 to the VAD 104), a connecting step while connecting the VAD 104 to an infusion bag 126 containing the prepared infusate 102, or an initiating step of infusing the prepared infusate 102 into the patient P through the infusion lumen 116.

Methods

Methods include is a method of the infusion system 100 such as in-line disinfection of a prepared infusate (e.g., the prepared infusate 102) with UV light in real-time during an infusion of a patient (e.g., the patient P). Such a method can include one or more steps selected from a VAD-obtaining step, a VAD-connecting step, a light ring-placing step, a cable-connecting step, and an infusing step.

The VAD-obtaining step includes obtaining the VAD 104 of the infusion system 100. As set forth above, the VAD 104 includes the intracorporeal conduit 108, the one-or-more extracorporeal conduits 110 fluidly connected to the intracorporeal conduit 108, the hub 112 between the proximal portion of the intracorporeal conduit 108 and the one-or-more respective distal portions of the one-or-more extracorporeal conduits 110, and the one-or-more respective connectors 114 of the one-or-more extracorporeal conduits 110.

If the UV light ring 106 is not integrated with the VAD 104 or fixedly coupled thereto, the method can include the light ring-placing step. The light ring-placing step includes placing the UV light ring 106 over the abluminal surface of the intracorporeal conduit 108, the extracorporeal conduit, the hub conduit, or the connector, thereby removably coupling the UV light ring 106 to the VAD 104. As set forth above, the UV light ring 106 can be configured to automatically adjust its size in accordance with the size of the intracorporeal conduit 108, the extracorporeal conduit, the hub conduit, or the connector.

The VAD-connecting step includes connecting the VAD 104 to the infusion bag 126 containing the prepared infusate 102.

If the VAD 104 does not include the internal power source 120, or, as an alternative thereto, the method can include the cable-connecting step. The cable-connecting step includes connecting the electrical cable, if present, to an external power source. The electronic circuitry 122 between the electrical cable and the UV light ring 106 is configured to supply power to the UV light ring 106.

The infusing step includes infusing the patient P with a disinfected infusate. The disinfected infusate results from irradiation of the prepared infusate 102 within the infusion lumen 116 of the VAD 104 by the UV light from the UV light ring 106 encircling a portion of the infusion lumen 116. (See FIGS. 4 and 5.)

Notably, as set forth above, the VAD 104 can include the indicator light 124 operably connected to the electronic circuitry 122 for emitting visible light when the UV light ring 106 emits the UV light. The UV light ring 106 can be further configured to automatically emit the UV light upon an activation event selected from an assembly step while assembling the VAD 104, the VAD-connecting step while connecting the VAD 104 to the infusion bag 126, or initiation of the infusing step of infusing the patient P with the disinfected infusate.

While some particular embodiments have been disclosed herein, and while the particular embodiments have been disclosed in some detail, it is not the intention for the particular embodiments to limit the scope of the concepts provided herein. Additional adaptations or modifications can appear to those of ordinary skill in the art, and, in broader aspects, these adaptations or modifications are encompassed as well. Accordingly, departures may be made from the particular embodiments disclosed herein without departing from the scope of the concepts provided herein.

What is claimed is:

1. An infusion system for in-line disinfection of a prepared infusate with ultraviolet ("UV") light, the infusion system comprising:

a vascular access device ("VAD") including:
- an intracorporeal conduit configured to be percutaneously inserted into a patient;
- one or more extracorporeal conduits fluidly connected to the intracorporeal conduit, the one or more extracorporeal conduit configured to remain outside a body of the patient;
- a hub between a proximal portion of the intracorporeal conduit and one or more respective distal portions of the one or more extracorporeal conduits; and
- one or more respective connectors of the one or more extracorporeal conduits; and a powered UV light ring configured to emit the UV light, the powered UV light ring encircling a portion of an infusion lumen of the VAD to irradiate the prepared infusate within the infusion lumen with the UV light for infusing a disinfected infusate into the patient during an infusion of the patient, and the powered UV light ring incorporated into a luminal surface of the infusion lumen.

2. The infusion system of claim 1, wherein the powered UV light ring is integrated into a luminal surface of the intracorporeal conduit, an extracorporeal conduit of the one or more extracorporeal conduits, a hub conduit of one or more hub conduits respectively fluidly connecting the one-or-more extracorporeal conduits to the intracorporeal conduit, or a connector of the one or more connectors.

3. The infusion system of claim 1, the VAD further comprising a fixed or removable internal power source and electronic circuitry between the fixed or removable internal power source and the powered UV light ring configured to supply power to the powered UV light ring from the fixed or removable internal power source.

4. The infusion system of claim 3, further comprising an indicator light operably connected to the electronic circuitry, the indicator light configured to emit visible light when the powered UV light ring emits the UV light.

5. The infusion system of claim 1, further comprising an electrical cable configured to connect to an external power source and electronic circuitry between the electrical cable and the powered UV light ring to supply power to the powered UV light ring.

6. The infusion system of claim 1, wherein the powered UV light ring is configured to automatically emit the UV light upon an activation event selected from an assembly step while assembling the VAD, a connecting step while connecting the VAD to an infusion bag containing the prepared infusate, or an initiating step of infusing the prepared infusate into the patient through the infusion lumen.

7. The infusion system of claim 1, wherein the VAD is a catheter, the intracorporeal conduit, the one or more extracorporeal conduits, the hub, and the one or more connectors being a catheter tube, one or more extension legs, a catheter hub, and one or more Luer connectors, respectively.

8. The infusion system of claim 1, wherein the VAD is a Huber needle set, the intracorporeal conduit, the one or more extracorporeal conduits, the hub, and the one or more connectors being a needle, an extension tube, a needle hub, and a Luer connector, respectively.

9. The infusion system according to claim 1, wherein the powered UV light ring is integrated into a luminal surface of the intracorporeal conduit.

10. The infusion system according to claim 1, wherein the powered UV light ring is integrated into a luminal surface of an extracorporeal conduit of the one or more extracorporeal conduits.

11. The infusion system according to claim 1, wherein the powered UV light ring is integrated into a luminal surface of a hub conduit of one or more hub conduits respectively fluidly connecting the one or more extracorporeal conduits to the intracorporeal conduit, or a connector of the one or more connectors.

12. The infusion system according to claim 1, wherein the powered UV light ring is integrated into a luminal surface of a connector of the one or more connectors.

13. A method of an infusion system for in-line disinfection of a prepared infusate with ultraviolet ("UV") light, the method comprising:

obtaining a vascular access device ("VAD") of the infusion system, the VAD including:
- an intracorporeal conduit configured to be percutaneously inserted into a patient;
- one or more extracorporeal conduits fluidly connected to the one or more intracorporeal conduit, the extracorporeal conduit configured to remain outside a body of the patient;
- a hub between a proximal portion of the intracorporeal conduit and one or more respective distal portions of the one or more extracorporeal conduits; and
- one or more respective connectors of the one or more extracorporeal conduits;

inserting the intracorporeal conduit into the patient;

connecting the VAD to an infusion bag containing the prepared infusate; and infusing the patient with a disinfected infusate, the disinfected infusate resulting from irradiation of the prepared infusate within an infusion lumen of the VAD by the UV light emitted from a powered UV light ring, the powered UV light ring encircling a portion of the infusion lumen, and the powered UV light ring incorporated into a luminal surface of the infusion lumen.

14. The method of claim 13, wherein the powered UV light ring is integrated into a luminal surface of the intracorporeal conduit, an extracorporeal conduit of the one or more extracorporeal conduits, a hub conduit of one or more hub conduits respectively fluidly connecting the one or more extracorporeal conduits to the intracorporeal conduit, or a connector of the one or more connectors.

15. The method of claim 13, the VAD further comprising a fixed or removable internal power source and electronic circuitry between the fixed or removable internal power source and the powered UV light ring configured to supply power to the powered UV light ring from the fixed or removable internal power source.

16. The method of claim 15, wherein an indicator light operably connected to the electronic circuitry is configured to emit visible light when the powered UV light ring emits the UV light.

17. The method of claim 13, further comprising connecting an electrical cable to an external power source and electronic circuitry between the electrical cable and the powered UV light ring to supply power to the powered UV light ring.

18. The method of claim 13, wherein the powered UV light ring is configured to automatically emit the UV light upon an activation event selected from an assembly step while assembling the VAD, a connecting step while connecting the VAD to the infusion bag, or an initiating step of infusing the patient with the disinfected infusate.

19. The method of claim 13, wherein the VAD is a catheter, the intracorporeal conduit, the one or more extracorporeal conduits, the hub, and the one or more connectors being a catheter tube, one or more extension legs, a catheter hub, and one or more Luer connectors of the catheter, respectively.

20. The method of claim 13, wherein the VAD is a Huber needle set, the intracorporeal conduit, the one-or-more extracorporeal conduits, the hub, and the one or more connectors being a needle, an extension tube, a needle hub, and a Luer connector of the Huber needle set, respectively.

21. The method according to claim 14, wherein the powered UV light ring is integrated into a luminal surface of the intracorporeal conduit or a hub conduit of one or more hub conduits respectively fluidly connecting the one-or-more extracorporeal conduits to the intracorporeal conduit.

22. The method according to claim 14, wherein the UV light ring is integrated into a luminal surface of an extracorporeal conduit of the one or more extracorporeal conduits or a connector of the one or more connectors.

* * * * *